United States Patent [19]

Volkmann

[11] Patent Number: 4,631,345

[45] Date of Patent: Dec. 23, 1986

[54] THIAZOLE PRECURSORS FOR THE PREPARATION OF BIOTIN

[75] Inventor: Robert A. Volkmann, Ledyard, Conn.

[73] Assignee: Pfizer Inc., New York, N.Y.

[21] Appl. No.: 807,064

[22] Filed: Feb. 18, 1986

Related U.S. Application Data

[62] Division of Ser. No. 587,757, May 17, 1984, Pat. No. 4,581,459, which is a division of Ser. No. 379,247, May 17, 1982, Pat. No. 4,468,516.

[51] Int. Cl.$^4$ ................. C07D 277/10; C07D 471/10; C07D 513/10; C07D 277/60
[52] U.S. Cl. ..................................... 548/147; 546/19; 548/110; 548/146
[58] Field of Search ...................... 548/147, 146, 110; 546/19

[56] References Cited

U.S. PATENT DOCUMENTS 2,865,924  12/1958  Asinger et al. ...................... 548/147

Primary Examiner—Richard A. Schwartz
Attorney, Agent, or Firm—Charles J. Knuth; Peter C. Richardson; Gezina Holtrust

[57] ABSTRACT

A novel process is described for preparation of biotin comprising preparation of substituted 3H, 5H-imidazo[1, 5c]tetrahydro thiazoles by contacting the boron triflouride adduct of an appropriate thiazoline with the metallic derivative of an ester enolate, reducing the ester, hydrolyzing the thiazolidine moiety and hydrolyzing or oxidizing the resultant compound. Intermediates obtained in the preparation of biotin by the above process and alternate procedures for preparing said intermediates are also presented. A novel process for preparation of d-biotin is also given.

5 Claims, No Drawings

THIAZOLE PRECURSORS FOR THE PREPARATION OF BIOTIN

This is a division of application Ser. No. 587,757, filed on May 17, 1984, now U.S. Pat. No. 4,581,459, which is a division of application Ser. No. 379,247, filed May 17, 1982, now U.S. Pat. No. 4,468,516.

BACKGROUND OF THE INVENTION

Biotin is a water-soluble vitamin required by higher animals and by many microorganisms. Biosynthesis of biotin by selected yeasts, molds and bacteria is well known. U.S. Pat. No. 3,393,129 reports the use of a d-biotin-producing strain of bacteria of the genus Sporobolomyces for commercial production of this vitamin. Chemical synthesis is reported in U.S. Pat. Nos. 2,489,235; 2,489,236; 4,029,647 and 4,124,595.

As industrial demand for d-biotin increases, the search for improved synthetic processes continues.

SUMMARY OF THE INVENTION

The present invention relates to a novel process for the preparation of biotin and novel intermediates useful therein.

One class of intermediates of the present invention are novel compounds of formula II

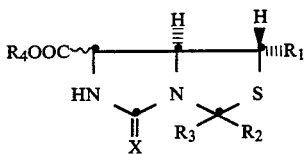

wherein
X is sulfur or oxygen;
$R_1$ is —$(CH_2)_4CH_3$, or
—$(CH_2)_3OR$ or —$(CH_2)_5OR$ wherein R is alkyl, or
—$(CH_2)_4CN$, or
—$(CH_2)_4COOR'$ wherein R' is alkyl or phenyl;
$R_2$ and $R_3$ when taken together are cycloalkyl or —$CH_2$—$CH_2$—Y—$CH_2$—$CH_2$ wherein Y is sulfur, oxygen or NR" wherein R" is COOR''' wherein R''' is alkyl, or
$R_2$ and $R_3$ when taken separately, are each alkyl, cycloalkyl or phenyl, provided that $R_2$ and $R_3$ are not both phenyl;
$R_4$ is hydrogen, alkyl, alkoxyalkyl, cycloalkyl, monoalkyl, substituted cycloalkyl, phenyl or mono-, di or trialkyl substituted phenyl; and
when $R_4$ is hydrogen, the addition salts thereof;
said alkyl and alkoxy having from 1 to 4 carbon atoms and said cycloalkyl having from 5 to 7 carbon atoms.

Preferred compounds include those wherein $R_1$ is —$(CH_2)_4CH_3$ or —$(CH_2)_4COOR'$ wherein R' is alkyl; $R_2$ and $R_3$ when taken together are cycloalkyl, or $R_2$ and $R_3$ when taken separately are each alkyl; and $R_4$ is alkyl. Especially preferred of these compounds are those wherein $R_1$ is —$(CH_2)_4CH_3$ or —$(CH_2)_4COOCH_3$; $R_2$ and $R_3$ when taken together are cyclohexyl, or $R_2$ and $R_3$ taken separately are each methyl; and $R_4$ is ethyl.

Also within the scope of the present invention are intermediates useful for the preparation of thiazoles of formula II. Thus, the present invention includes compounds of formula I

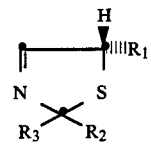

wherein
$R_1$, $R_2$ and $R_3$ are as previously defined;
$R_2$ and $R_3$ when taken together are cycloalkyl or —$CH_2$—$CH_2$—Y—$CH_2$—$CH_2$ wherein Y is sulfur, oxygen or NR" wherein R" is COOR''' wherein R''' is alkyl; or
$R_2$ and $R_3$ when taken separately are each alkyl, cycloalkyl or phenyl, provided that $R_2$ and $R_3$ are not both phenyl;
said alkyl having from 1 to 4 carbon atoms and said cycloalkyl having from 3 to 7 carbon atoms.

Also included in the present invention are the boron trifluoride adducts of compounds of formula I, especially those wherein
$R_1$ is —$(CH_2)_4CH_3$ or —$(CH_2)_4COOR'$ wherein R' is alkyl; and
$R_2$ and $R_3$ when taken together are cycloalkyl, or
$R_2$ and $R_3$ when taken separately are each alkyl.
Preferred compounds include those wherein
$R_1$ is —$(CH_2)_4CH_3$ or —$(CH_2)_4COOCH_3$; and
$R_2$ and $R_3$ when taken together are cyclohexyl, or
$R_2$ and $R_3$ when taken separately are each methyl.

The present invention also includes a process for the preparation of compounds of formula II comprising contacting a boron trifluoride adduct of a compound of formula I with a compound of the formula

wherein
A is —N=C=O, —N=C=S, —N=S=O, —N̄—$CO_2R_7$, or —N=C(H)$R_7$ wherein $R_7$ is alkyl or phenyl;
M is a metal selected from lithium, sodium, potassium, zinc, magnesium or zirconium or a counterion of the formula N($R_8$)$_4^+$ or B($R_8$)$_2$ wherein $R_8$ is an alkyl group having from 1 to 4 carbon atoms; and
$R_4$ is as previously defined.

A further class of intermediates useful in the process of the present invention are novel compounds of formula III

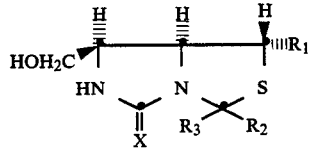

wherein X, $R_1$, $R_2$ and $R_3$ are as previously defined.

Preferably $R_1$ is —$(CH_2)_4CH_3$ or —$(CH_2)_4COOR'$ wherein R' is alkyl; $R_2$ and $R_3$ when taken together are cycloalkyl, or $R_2$ and $R_3$ when taken separately are each alkyl. Especially preferred are compounds wherein
$R_1$ is —$(CH_2)_4CH_3$ or —$(CH_2)_4COOCH_3$; and
$R_2$ and $R_3$ when taken together are cyclohexyl or
$R_2$ and $R_3$ when taken separately are each methyl.

Further intermediates of the present invention are novel compounds of formula IV

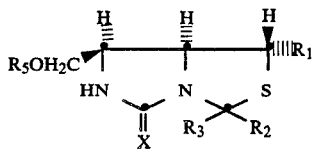

wherein
X, $R_1$, $R_2$ and $R_3$ are as previously defined; and
$R_5$ is —C(O)$R_6$ or —SO$_2R_6$ wherein is alkyl, haloalkyl, phenyl or mono- or dialkyl substituted phenyl or camphoryl; said alkyl having from 1 to 4 carbon atoms and said cycloalkyl having from 5 to 7 carbon atoms.

Preferred compounds include those wherein
$R_1$ is —(CH$_2$)$_4$CH$_3$ or —(CH$_2$)$_4$COOR' wherein R' is alkyl;
$R_2$ and $R_3$ when taken together are cycloalkyl, or
$R_2$ and $R_3$ when taken separately are each alkyl; and
$R_5$ is acetyl, mesyl, tosyl or camphorsulfonyl.
Especially preferred are compounds wherein
$R_1$ is —(CH$_2$)$_4$CH$_3$ or —(CH$_2$)$_4$COOCH$_3$; and
$R_2$ and $R_3$ when taken together are cyclohexane or
$R_2$ and $R_3$ when taken separately are each methyl; and
$R_5$ is —SO$_2R_6$ wherein $R_6$ is d-10-camphoryl.

Further intermediates of the present invention are novel compounds of formula V

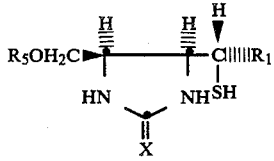

wherein X and $R_1$ are as previously defined and $R_5$ is as previously defined or hydrogen.

Preferred compounds include those wherein
$R_1$ is —(CH$_2$)$_4$CH$_3$ or —(CH$_2$)$_4$COOCH$_3$; and
$R_5$ is hydrogen, acetyl, mesyl, tosyl or camphorsulfonyl. Especially preferred are compounds wherein $R_1$ is —(CH$_2$)$_4$CH$_3$ and $R_5$ is d-10-camphorsulfonyl or hydrogen.

Further intermediates of the present invention are those of formula VI

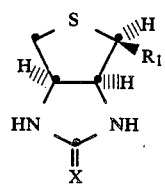

wherein X and $R_1$ are as previously defined, provided that when $R_1$ is (CH$_2$)$_4$COOR', R' is alkyl having from 2 to 4 carbon atoms, Also included in the present invention are processes for preparation of compounds of Formula VI by cyclizing intermediate compounds of formula V.

Further intermediates of the present invention are compounds of the formula

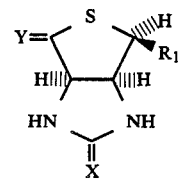

wherein X and $R_1$ are as previously defined and Y is =O, formula VIII, or Y is —H and —OH, formula IX.

Compounds VI may also be prepared by reducing a thiolactone of formula VIII in a reaction inert solvent with an alkali metal borohydride followed by treatment with an electropositive metal in the presence of an acid.

Compounds VI wherein X is sulfur may be converted to the oxygen analog by contacting it with a haloalcohol in the presence of weak base in a protic solvent.

The present invention further comprises a method for preparation of biotin comprising contacting in solution a compound of formula IIA with an alkali metal borohydride followed by the addition of water, treating the resultant compound of formula III with strong aqueous acid or with an alkyl or aryl sulfonyl halide or acyl halide in the presence of base, and contacting these products with strong aqueous acid, and, when X is sulfur, refluxing with a haloalcohol. The resultant compound may be hydrolyzed, treated with acid followed by sodium diethyl malonate and then hydrolyzed, or oxidized depending on the nature of the $R_1$ group to form biotin.

In a preferred process of this invention, d-biotin may be prepared by resolving an acid of formula IIA with (d)- ephedrine, separating the resultant diastereometric mixture of compounds, esterifying the requisite stereoisomer to give a compound of formula II wherein $R_4$ is methyl, contacting this ester with borohydride and then acid, and when X is sulfur, treating the resultant bicyclic thiourea with a haloalcohol, and hydrolyzing or oxidizing, as appropriate in view of the nature of the $R_1$ group, to form biotin.

DETAILED DESCRIPTION OF THE INVENTION

The present invention relates to the synthesis of biotin from the intermediates described above as shown in Schemes A and B to which reference is made for the following discussion. The formulae given in these Schemes and throughout the present application conform to the accepted convention for indicating stereoisomers, namely, " ⅠⅠⅠⅠⅠⅠ " to indicate an atom projecting into the plane of the paper (α-orientaton) "—" to indicate an atom projecting out from the plane of the paper (β-orientation) and hence the plane of the molecule itself and "⌇" to indicate a substituent which is in either the α or β-orientation. Numbering of compounds throughout this application follows the sequence given in Schemes A and B. It will be appreciated that $R_2$, $R_3$ and $R_4$ groups in the compounds of formulae I to V are protecting groups which will be subsequently removed in later reaction steps. Likewise $R_5$, $R_6$, R, R', R" and R'" are intermediate groups in the synthesis of the final compounds. Accordingly, while intermediates having $R_2$, $R_3$, $R_4$, $R_5$, $R_6$, R, R', R" and R'" substituents as previously defined are preferred for use in the present invention, the use of such substituents is not critical and other similar protecting and intermediate substituent groups may be employed in the present process to obtain biotin. For example, higher alkyl or cycloalkyl groups, up to about 17 carbon atoms, may be employed, together with substituted aryl groups, such as phenyl substituted with alkyl, halo, nitro or alkoxy groups, or naphthyl.

Substituted 3H,5H-imidazo[1,5c]tetrahydrothiazoles of formula II may be prepared by contacting in a non-protic solvent at about $-100°$ C. to $-30°$ C. the boron trifluoride adduct of a compound of formula I, wherein $R_1$, $R_2$ and $R_3$ are as previously defined, with the metallic derivatives of an ester enolate of the formula

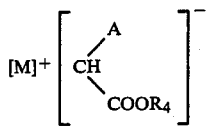

wherein M+ is lithium, sodium, potassium, zinc, magnesium or zirconium or a counterion of the formula $N(R_8)_4^+$ or $B(R_8)_2$ wherein $R_8$ is an alkyl group having from 1 to 4 carbon atoms and A is $-N=C=O$ or $-N=C=S$. Compounds wherein A is as defined are preferred for use in the present invention, but it will be appreciated that similar protecting groups may be employed to make the intermediates useful for the preparation of biotin by the process of the present invention, for example compounds wherein A is $-N=S=O$, $-N-COOR$ wherein R is alkyl or $-N=C(H)R_7$ wherein $R_7$ is phenyl.

More particularly, compounds of formula II wherein $R_1$ is $-(CH_2)_4CH_3$ or $-(CH_2)_4COOR'$ wherein R' is alkyl, $R_2$ and $R_3$ when taken together are cycloalkyl or $-CH_2-CH_2-N(R'')-CH_2-CH_2-$ wherein R'' is $-COOR'''$ wherein R''' is alkyl or $R_2$ and $R_3$ separately are each alkyl, cycloalkyl or phenyl provided that $R_2$ and $R_3$ are not both phenyl; and $R_4$ is alkyl or phenyl may be prepared by contacting in a non-protic solvent, preferably tetrahydrofuran, the boron trifluoride adduct of a compound of formula I wherein $R_1$ is $-(CH_2)_4CH_3$ or $-(CH_2)_4$ $CO_2R'$ wherein R' is alkyl and $R_2$ and $R_3$ are as given above, at a temperature between about $-100°$ C. to $-0°$ C. preferably near $-78°$ C. with a metallo derivative of an ester enolate of the formula

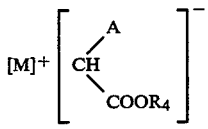

wherein [M] is lithium, sodium, potassium, zinc or magnesium, but most preferably lithium;

A, when X of the resultant compound of formula II is oxygen, is $-N=C=O$ or A, when X of said compound of formula II is sulfur, is $-N=C=S$; and $R_4$ is alkyl or phenyl.

Preferred compounds which may be prepared by this method include those wherein $R_1$ is $-(CH_2)_4CH_3$ or $-(CH_2)_4COOCH_3$, $R_2$ and $R_3$ when taken together are cycloalkyl, preferably cyclohexyl or $-CH_2-CH_2-Y-CH_2-CH_2-$ wherein Y is NR'' wherein R'' is $-COOR'''$ wherein R''' is alkyl, preferably methyl or ethyl, $R_2$ and $R_3$ when taken separately are alkyl, preferably methyl or ethyl or $R_2$ and $R_3$ when taken together are cycloalkyl, preferably cyclohexyl and $R_4$ is alkyl, preferably ethyl, n-propyl or isopropyl, alkoxy, preferably ethylmethoxy or alkyl substituted phenyl, preferably 2,6-di-t-butyl-4-methyl phenyl or 2-methyl-6-t-butylphenyl or cycloalkyl such as norboronyl.

The boron trifluoride adduct of the compound of formula I may be prepared by combining in a suitable non-polar solvent, preferably tetrahydrofuran, said thiazoline of formula I and an essentially equimolar amount of boron trifluoride diethyl ether at a temperature between about $-78°$ C. and $30°$ C. preferably about $0°$ C.

The metallo derivative of ester enolate may be prepared by standard methods such as combining in a suitable non-polar solvent, preferably tetrahydrofuran at temperatures between about $-100°$ C. and $10°$ C. preferably $-78°$ C. an alkyl isocyanatoacetate and a metallo dialkylamide, for example lithium diisopropylamide, which in turn is generated by adding butyllithium to a dialkylamine solution. In the case of an alkyl or phenyl isothiocyanatoacetate, either a metallo dialkylamide preferably lithium di-isopropylamide or a metallo alkoxide, preferably lithium t-butoxide can be used to generate the metallo derivatives of the ester enolates. The nature of the alkyl or aryl substitutent ($R_4$) present in the isothiocyanatoacetate influences the ratio of products of formulas IIA:IIB formed. For example, the ratio of IIA:IIB is 1.3:1 when methyl isothiocyanatoacetate is used and with ethyl isothiocyanatoacetate, the ratio of IIA:IIB is 3:1. Since IIA is the desired isomer in the synthesis of biotin, compounds in which $R_4$ is ethyl are preferred.

The desired compound of formula IIA can be separated from formula IIB by standard chromatographic processes or by crystallization. The compounds of formula IIA are employed in the further synthesis of biotin.

3-Thiazolines of formula I may, in turn, be prepared according to the method of Thiel, Asinger and Schmiedel (Liebigs Ann. Chem. 611 121 (1958)) wherein 2-bromoaldehydes, compounds easily synthesized by known methods, of the formula

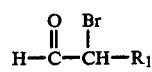

wherein $R_1$ is as defined, is combined with sodium hydrogen sulfide and then with a carbonyl compound of the formula

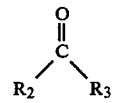

wherein $R_2$ and $R_3$ are as defined, followed by the addition of ammonia.

Compounds of formula I, for example, which may be prepared by this method, are those wherein $R_1$ is preferably $-(CH_2)_4CH_3$ or $-(CH_2)_4COOCH_3$; and $R_2$ and $R_3$ together are preferably cyclohexyl or $R_2$ and $R_3$ separately are each methyl.

The desired enantiomer of the compound of formula IIA required for a synthesis of d-biotin can be obtained by a resolution of racemic mixtures of IIA in which $R_4=H$. The overall procedure may be accomplished, for example, by a saponification of the racemic ester IIA obtained in the imine addition reaction to form a racemic acid which when treated with a chiral base, may be separated into diasteriometric salts, which once separated may be converted to optically pure esters of formula IIA. More specifically, racemic ester IIA ($R_4=CH_2CH_3$) may be saponified to the corresponding racemic acid of formula IIA ($R_4=H$) upon treatment with an alkali hydroxide such as sodium hydroxide in a polar solvent such as methanol or tetrahydrofuran. Treatment of racemic acid of formula IIA with an optically pure base such as d-ephedrine in a polar solvent such as ether generates a solid which can be crystallized in an optically pure form. Treatment of this salt, for example, with an alcoholic solvent in the presence of acid such as methanolic hydrogen chloride generates optically pure ester of formula IIA wherein $R_4$ is methyl.

Compounds of formula III, 7-hydroxymethyl-3H,5H-imidazo[1,5c]tetrahydrothiazoles, may be prepared by contacting esters of formula IIA wherein $R_4$ is preferably ethyl or methyl in a polar solvent, preferably methanol, ethanol or tetrahydrofuran with a borohydride derivative, an alkali metal borohydride for example, wherein the alkali metal is preferably sodium, at a temperature between $-10°$ C. and $25°$ C. for a period of about 1-5 hours followed by addition of water.

Alternatively, optically pure acids of formula IIA may be reduced with diborane to generate III directly.

Compounds of Formula III may then be converted directly to the biotin ring structure of formula VI via intermediate V. For example, alcohol III is treated with a strong acid at elevated temperatures to generate VI directly. In particular, compounds of formula VI wherein $R_1$ is $-(CH_2)_4CH_3$ or $-(CH_2)_4CO_2H$ and X is O or S may be prepared by contacting alcohol III, wherein $R_1$ is $-(CH_2)_4CH_3$ or $-(CH_2)_4CO_2R'$ wherein $R'$ is preferably methyl, $R_2$ and $R_3$ when taken together are cyclohexyl, or when taken separately are alkyl preferably methyl with aqueous trifluoroacetic acid or methanesulfonic acid at temperature between about $40°$ to $105°$ C. until reaction is substantially complete.

Alternatively, compounds of formula III may be converted to compounds of formula IV by contacting compounds of formula III with a sulfonyl or acyl halide in a polar solvent in the presence of a base, preferably trialkylamine.

Thus compounds of formula IV wherein $R_5$ is $SO_2R_6$ or $COR_6$ wherein $R_6$ is alkyl or haloalkyl, most preferably methyl, tolyl or camphoryl are prepared by contacting III wherein $R_1$ is $-(CH_2)_4CH_3$ or $-(CH_2)_4CO_2R'$, $R_2$ and $R_3$ when taken together are cyclohexyl or when taken separately are alkyl, preferably methyl, in a solvent such as methylene chloride with triethylamine and an appropriate sulfonyl chloride at temperatures between about $-78°$ to $25°$ C. When racemic III is treated with an optically active sulfonyl chloride, a diastereomeric mixture results which may be separated to afford optically pure compounds of formula IV of the desired chirality. For example, compound IV wherein $R_5$ is $SO_2R_6$ and $R_6$ is d- or l-10-camphoryl and $R_1$ is $(CH_2)_4CH_3$ and $R_2$ and $R_3$ when taken together are cyclohexyl can easily be separated by means of silica gel chromatography to give the desired pure diastereomer of formula IV.

Compounds of formula IV may then be converted directly to the biotin ring structure by treating compounds of formula IV wherein $R_5$ is acyl or sulfonyl in a strong acid at elevated temperatures. For example, the d-biotin framework of VI in which $R_1$ is $(CH_2)_4CH_3$ may be generated by treating the requisite camphorsulfonate of formula IV in which $R_1$ is $(CH_2)_4CH_3$, $R_2$ and $R_3$ taken together are cyclohexyl, $R_5$ is $SO_2R_6$ and $R_6$ is d-10-camphor with aqueous trifluoroacetic acid at temperature between about $35°$ to $105°$ C. for 1 to 24 hours.

Compounds of formula VI wherein X is S may be converted to the oxygen analogue by contacting the corresponding thiourea derivative of formula VI wherein X is sulfur with a haloalcohol, preferably bromoethanol, in an polar solvent such as ethanol, methoxyethanol or diglyme, and refluxing under inert gas, preferably nitrogen, until reaction is essentially complete, from 2 to 24 hours, and then treating with a weak base, an alkali metal carbonate for example, preferably a saturated solution of sodium carbonate.

The conversion of compound VI wherein X is O and $R_1$ is $(CH_2)_4CH_3$ to biotin may be accomplished by a microbiological oxidation. The preferred microbiological oxidation is that disclosed in Ogino et al in U.S. Pat. No. 3,859,167, the disclosure of which is incorporated herein by reference. Accordingly, biotin wherein $R_1$ is $(CH_2)_4CO_2H$ is obtained upon treatment of VI wherein $R_1$ is $(CH_2)_4CH_3$ and X is oxygen with the organism *Corynebacterium primorioxydans*. Compound VI wherein X is S and $R_1$ is $-(CH_2)_4CH_3$ may likewise be converted by microbiological oxidation by an organism such as *Corynebacterium primorioxydans* to the sulfur analog of biotin.

A novel process is also herein presented for preparation of intermediate compounds of formula VI by reduction of the corresponding thiolactone of formula VIIIA as shown in Scheme B wherein $R_1$, $R_2$, $R_3$, $R_4$ and X are as previously defined.

As shown in Scheme B, thiolactones of formula VIIIA wherein $R_1$ is $(CH_3)_4CH_3$ may be prepared by:

contacting a compound of the formula IIA wherein $R_1$ is $-(CH_2)_4CH_3$, $R_2$ and $R_3$ are each alkyl, preferably methyl, and $R_4$ is alkyl, preferably ethyl, with a strong acid, preferably aqueous trifluoroacetic acid at a temperature between $80°$ to $120°$ C., preferably about $100°$ C.; or contacting a compound of the formula IIA in a polar solvent, for example, aqueous methanol, with an essentially equimolar amount of base, preferably an alkali metal hydroxide, for a period of about 5 to 12 hours at a temperature between $20°$ C. to $35°$ C. followed by acidification to a pH between 2.0 to 3.0, preferably about 2.5 with an aqueous acid halide, preferably hydrochloric acid; and contacting the resultant carboxylic acid with acid, preferably trifluoroacetic acid with an excess molar amount of water at a temperature between $45°$ C. to $55°$ C. for about 6 to 8 hours.

Alternatively, compounds of formula VIIIA may be prepared by:

contacting IIB in a polar solvent, for example, aqueous methanol, with an essentially equimolar amount of base, preferably an alkali metal hydroxide, for a period of 1 to 2 hours at a temperature of $-0°$-$10°$ C. followed by acidification to a pH between 2.0 to 3.0, preferably about 2.5 with an aqueous acid halide, preferably hydrochloric acid;

contacting the resultant acid with acid, preferably trifluoroacetic acid in an excess molar amount of water at a temperature of about $15°$ C.-$35°$ C. for 2 to 3 hours;

contacting the resultant thiol VIIB in a polar solvent, preferably methylene chloride, with a basic trialkylamine, preferably triethylamine followed by an alkylhaloformate, preferably ethyl chloroformate at a temperature between about 15° C. to 35° C. for a period of 2 to 3 hours to give lactone VIIIB which may be converted to VIIIA by contacting VIIB in a polar solvent, preferably tetrahydrofuran, with a non-nucleophalic base, for example.

Intermediate compounds of formula VIIIA may be converted to intermediate compounds of formula VI by reduction. Compounds of formula VI, for example, wherein $R_1$ is preferably $-(CH_2)_4CH_3$ or $-(CH_2)_4COOCH_3$ may be prepared by contacting a thiolactone of formula VIIA wherein $R_1$ is $-(CH_2)_4CH_3$ or $-(CH_2)_4COOCH_3$ in a polar solvent, preferably methanol at a temperature between $-10°$ C. to 25° C., preferably about 0° C. with a metallic borohydride, preferably sodium borohydride for a period of about one hour and contacting the resultant hemiacetal in acid solution with zinc metal under reflux for a period of 12 to 48 hours, until reduction is essentially complete.

SCHEME A

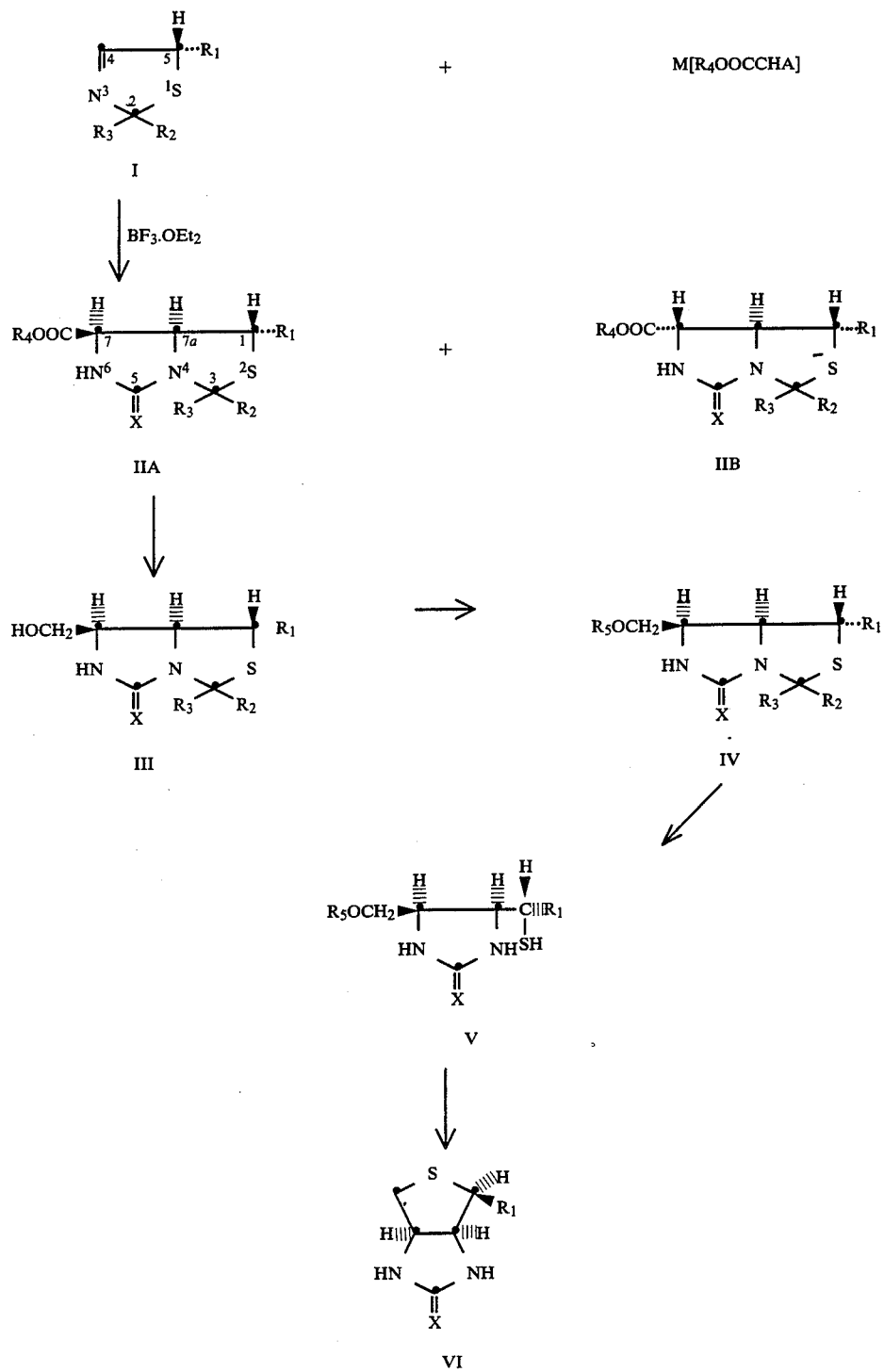

4,631,345
-continued
SCHEME A
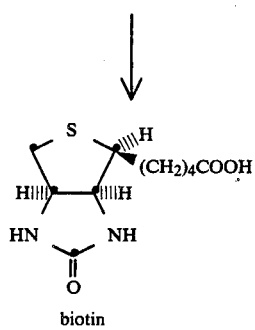
biotin
SCHEME B
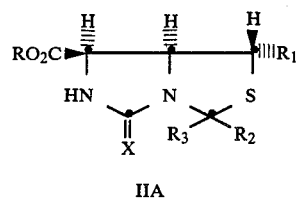   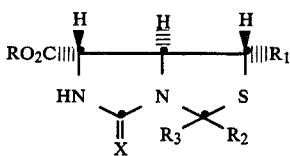
IIA                     IIB
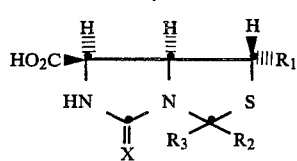   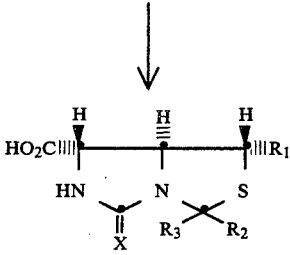
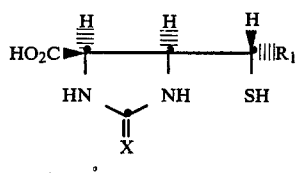   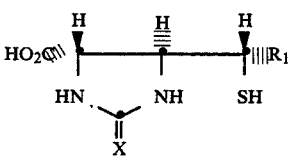
VIIA                    VIIB
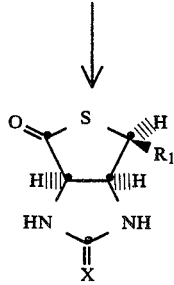   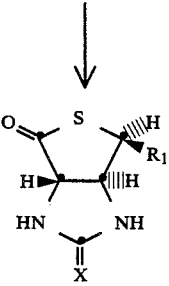
VIIIA                   VIIIB

SCHEME B

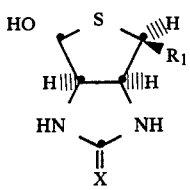

IX

↓

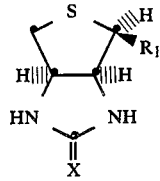

VI

The present invention is illustrated by the following examples. It should be understood, however, that the invention is not limited to the specific details of these examples.

EXAMPLE 1

3H,5H-Imidazo[1,5c]thiazole-7-carboxylic acid, tetrahydro-3,3-dimethyl-5-oxo-1-pentyl-, ethyl ester (1α,7α,7aα) and (1α,7β,7aα).

To a tetrahydrofuran solution (50 ml) containing 2,2-dimethyl-5-pentyl-3-thiazoline (5.58 grams, 30.2 mmole) at 0° C. was added boron trifluoride etherate (3.70 ml, 30.2 mmol) over a one minute period. Solution was allowed to warm to room temperature and stirred for one hour and then cooled to −78° C. Diisopropylamide was prepared by adding 2.3M m-butyllithium (13.1 ml, 30.2 mmol) to diisopropylamine (4.24 ml, 30.2 mmol) in tetrahydrofuran (300 ml) at −78° C. and stirring for 60 minutes. To this solution was added dropwise over a period of 1 minute, ethylisocyanoacetate (3.90 grams, 30.2 mmol). This solution was stirred at −78° C. for 5 minutes and then was added over a 1 minute period to the boron trifluoridethiazoline solution. The mixture was stirred at −78° C. for two hours, allowed to warm gradually to room temperature and stirred for another 1 hour. The reaction mixture was concentrated. Ethyl acetate was added and the organic solution was extracted with 0.5N HCL, dried over magnesium sulfate and concentrated in vacuo. The crude product was purified by column chromatography on silica gel (eluant methylene chloride:ether, 3:2) to give 4.69 g (50%) of a product mixture (1:1) containing 3H,5H-imidazo[1,5c]-thiazole-7-carboxylic acid, tetrahydro-3,3-dimethyl-5-oxo-1-pentyl ethylester (1α,-7α,7aα) MP 71°–73°.

IR (KBr) 3267, 2926, 1731, 1704; NMR (d, CDCL₃) 0.6–2.4 (20H, m, CH₃, CH₂) 3.2–3.7 (1H, m, CHS), 3.9–4.6 (4H, m, CHN, CHN, OCH₂), 5.1–5.4 (1H, m, NH).

Analysis Calculated for $C_{15}H_{26}O_3N_2S$: C, 57.32; H, 8.28, N, 8.92. Found: C, 56.97; H, 8.12; N, 8.87; And 3H,5H-Imidazo[1,5c]thiazole-7-carboxylic acid, tetrahydro-3,3-dimethyl-5-oxo-1-pentyl-, ethylester (1α,7β,7aα), MP 74°–75° C. (IR (KBr) 3280, 3926, 1731, 1705; NMR (d, CDCL₃) 0.66–2.25 (2H, m, CH₃CH₂) 3.0–3.5 (1H, m, CHS), 3.9–4.6 (4H, m, CHN, CHN, OCH₂), 5.3–5.6 (1H, m, NH)

Analysis Calculated for $C_{15}H_{26}O_3N_2S$: C, 57.32; H, 8.28; N, 8.92; S, 10.19; Found: C, 57.47; H, 8.28; N, 8.97; S, 10.18.

EXAMPLE 2

3H,5H-Imidazo[1,5c]thiazole-7-carboxylic acid, tetrahydro-3,3-dimethyl-5-thioxo-1-pentyl-, ethyl ester (1α,7α,7aα) and (1α,7β,7aα)

2,2-Dimethyl-5-pentyl-3-thiazoline (860 mg, 4.65 mmol) was dissolved in tetrahydrofuran (20 ml) and cooled to 0° C. Boron trifluoride etherate (0.510 ml, 4.65 mmol) was added over a one minute period. The solution was allowed to warm to room temperature for about 1.25 hour and then cooled to −78° C. In a separate flask was placed diisopropylamine (0.652 ml, 4.65 mmol) followed by tetrahydrofuran (10 ml). The solution was cooled to −78° C. 1.5M butyl lithium (3.1 ml, 4.65 mmol) was added over a 5 minute period. The solution was stirred at −78° for one hour. To this solution was added ethyl isothiocyanotoacetate (674 mg, 4.65 mol) in tetrahydrofuran (5 ml) over a 5 minute period. The solution was stirred for 25 minutes at −78° C. and was then added to the boron trifluoride thiazoline solution. The solution was stirred at −78° for 2 hours and quenched with acetic acid (266 ml, 4.66 mmol). The solution was allowed to warm to room temperature, concentrated in vacuo and was taken up in methylene chloride. This organic solution was washed with aqueous bicarbonate, dried over MgSO₄ and concentrated to afford a black oil which was purified by column chromatography on pH 9 silica gel (eluant methylene chloride:ether, 20:1) to give 1.030 g (67%) of a product mixture containing 278 mg (18%) of 3H,5H-imidazo[1,5c]thiazole-7-carboxylic acid, tetrahydro-3,3-dimethyl-5-thioxo-1-pentyl; ethylester (1α,7β,7aα) which formed needles after a methanol recrystallization, mp 123–124.5. IR (KBr) 3207, 2933, 1743; NMR (d, CDCL₃) 0.6–2.4 (20H, m, CH₂, CH₃), 3.2–3.8 (1H, m, CHS), 4.0–4.8 4H, M, CHN, CH₂—O), 6.8–7.0 (1H, m, NH). Analysis Calculated for C$_{15}$H$_{26}$O$_2$N$_2$S$_2$: C, 54.51: H, 7.93; N, 8.48. Found C, 54.44; H 7.80; N 8.62; and 752 mg (49%) of 3H,5H-imidazo[1,5c]-thiazole-7-carboxylic acid, tetrahydro-3,3-dimethyl-5-thioxo-1-pentyl; ethylester (1α,7β,7aα) which was crystallized from ether, MP 106°–107° C. IR (KBr) 3437, 2925, 1743; NMR (d, CDCl$_3$) 0.6–2.3 (20H, m, CH$_2$, CH$_3$), 3.0–3.6 (1H, m, CHS). 4.0–4.9 (4H, m, CHN, CH$_2$O), 6.3–6.5 (1H, m, NH). Analysis Calculated for C$_{15}$H$_{26}$O$_2$N$_2$S$_2$: C, 54.51; H, 7.93; N, 8.48. Found C, 54.23; H, 7.71; N, 8.63.

EXAMPLE 3

3H,5H-Imidazo[1,5c]thiazole-1-pentanoic acid, tetrahydro-7-carboethoxy-3,3-dimethyl-5-oxo, methyl ester, (1α,7α,7aα) and (1α,7β,7aα)

To 2,2-Dimethyl-3-thiazole-5-pentanoic acid, methyl ester (5.77 g, 23 mmol) in dry tetrahydrofuran (50 ml) at 0° C. was added over a one minute period boron trifluoride etherate (2.82 ml, 23 mmol). The reaction mixture was allowed to warm to room temperature, stirred for one hour, and cooled to −78° C. To an addition funnel containing diisopropylamine (3.23 ml, 23 mmol) at room temperature in tetrahydrofuran (150 ml) was added 2.3M butyl lithium (10 ml, 23 mmol). The solution was stirred at room temperature for 15 minutes and then cooled to −78° C. To this solution was added all at once ethyl isocyanatoacetate (2.97 g, 23 mmol) in tetrahydrofuran (10 ml). This solution was allowed to stir for 6 minutes and then added to the boron trifluoride-thiazoline solution. The resulting solution was stirred at −78° for 2 hours and allowed to warm to room temperature and stirred for about 20 minutes. The reaction mixture was concentrated, taken up in ethyl acetate and extracted with 0.5N hydrochloric acid solution. The aqueous layer was back extracted with ethyl acetate (3×). The organics were washed with brine, dried over magnesium sulfate, concentrated to afford 9.8 grams of crude product which was chromatographed on 330 grams of silica gel using methylene chloride:diethyl ether (3:2) to afford 3.05 g (37%) of a product mixture (1:1) containing 3H,5H-imidazo[1,5c]thiazole-1-pentanoic acid, tetrahydro-7-carboethoxy-3,3-dimethyl-5-oxo; methylester, (1α,7α,7aα) as an oil. IR (CHCl$_3$) 3444, 2926, 1726; NMR (d, CDCL$_3$) 1.1–2.1 (15H, m, CH$_2$, CH$_3$), 2.2–2.6 (2H, m, CHCH$_2$), 3.3–3.6 (1H, m, CHS), 3.7 (3H, s, OCH$_3$), 4.0–4.6 (4H, m, CHN, OCH$_2$), 5.1–5.3 (1H, m, NH). Analysis Calculated for C$_{16}$H$_{26}$O$_5$N$_2$S: C, 53.61; H, 7.31; N, 7.81; S, 8.94. Found: C, 53.32; H, 7.26; N, 8.06; S, 8.57; and 3H,5H-Imidazo[1,5c]-thiazole-1-pentanoic acid, tetrahydro-7-carboethoxy 3,3-dimethyl-5-oxo-methyl ester, (1α,7β,7aα), mp 89°–90° C. IR (KBr) 3242, 2928, 1746, 1700; NMR (d, CDCl$_3$) 0.63–2.1 (15H, m, CH$_2$, CH$_3$), 2.13–2.6 (2H, m, CHCH$_2$), 3.1–3.5 (1H, m, CHS) 3.7 (3H, s, OCH$_3$), 3.9–4.6 (4H, m, CHN, OCH$_2$); 4.9–5.2 (1H, m, NH). Analysis Calculated for C$_{16}$H$_{26}$O$_5$N$_2$S: C, 53.61; H, 7.31; N, 7.81; S, 8.94. Found: C, 53.81; H, 7.52; N, 7.75; S, 8.88.

EXAMPLE 4

3H,5H-Imidazo[1,5c]thiazole-1-pentanoic acid, tetrahydro-7-carboethoxy-3,3-dimethyl-5-thioxo, methyl ester (1α,7α,7aα) and (1α,7β,7aα)

To a dry tetrahydrofuran solution (100 ml) containing 2,2-dimethyl-3-thiazoline-5-pentanoic acid, methyl ester (11.17 g, 48.8 mmol) under a nitrogen atmosphere at −4° C. was added dropwise over a 2 minute period boron trifluoride etherate (6.00 ml, 48.78 mmol). Internal temperature did not rise abot 0° C. The reaction mixture was stirred at −4° to 0° C. for 15 minutes. The ice bath was removed and the reaction mixture was stirred for 45 minutes and then cooled to −75° C.

Lithium t-butoxide (4.10 grams, 51.22 mmol) was dissolved in dry tetrahydrofuran (150 ml) and the solution was cooled to −75° C. Ethyl isothiocyanatoacetate (7.07 grams, 48.78 mmol) was dissolved in dry tetrahydrofuran (50 ml) in a cold jacketed addition funnel (−75° C.) and was added to the lithium t-butoxide solution over 6 to 7 minutes. Internal temperature did not exceed −71° C. The solution was stirred for 10 minutes following the addition. A polyethylene tube was put into the anion solution and nitrogen was used to push the anion into the imine/boron trifluoride solution. The addition occurred in less than one minute. The internal temperature of the final reaction mixture rose from −75° to −65°. The reaction mixture was stirred at −75° C. for 1.5 hours and then quenched with acetic acid (2.8 ml, 48.78 mmol) in tetrahydrofuran (5 ml). The brown reaction mixture became light orange. Organic solvents were removed in vacuo and the residue was taken up in 900 ml of ethyl acetate and washed with 5×200 ml of sodium bicarbonate solution followed by 1×200 ml of brine. The organic portion was dried over magnesium sulfate, filtered and concentrated in vacuo to afford 18.22 grams of product. The crude product was purified by column chromatography on pH 9 buffered silica gel (eluant methylene chloride:ether, 98:2) to give 14.80 g (81%) of a product mixture (1:2.5) containing 3H,5H-imidazo[1,5c]thiazole-1-pentanoic acid, tetrahydro-7-carboethoxy-3,3-dimethyl-5-thioxo, methyl ester (1α,7α,7aα) which could be recrystallized from hexane to give a solid, mp 55°–55.5° C. IR (KBr) 3211, 2929, 1740; NMR (d, CDCL$_3$) 1.1–2.6 (17H, m, CH$_2$CH$_3$, CH$_2$, CCH$_3$), 3.1–3.6 (1H, m, CHS), 3.7 (3H, S, OCH$_3$), 3.9–4.8 (4H, m, CHN, OCH$_2$), 6.5 (1H, n, NH). Analysis Calculated for C$_{16}$H$_{26}$N$_2$O$_4$S$_2$: C, 51.34; H, 6.95; N, 7.49. Found C, 51.23; H, 6.86; N, 7.26; and 3H,5H-imidazo[1,5c]thiazole-1-pentanoic acid, tetrahydro-7-carboethoxy-3,3-dimethyl-5-thioxo-methyl ester (1α,7β,7aα) which was recrystallized from hexane to give a solid, mp 76°–78° C. IR (KBr) 3439, 3411, 2940, 1740; NMR (d, CDCl$_3$) 1.1–2.7 (17H, m, CH$_2$CH$_3$, CH$_2$, CCH$_3$), 3.1–3.6 (1H, m, CHS), 3.7 (3H, s, OCH$_3$), 3.9–4.9 (4H, m, CHN, OCH$_2$), 5.19–6.3 (1H, m, NH). Analysis Calculated for C$_{16}$H$_{26}$N$_2$O$_4$S$_2$: C, 51.34; N, 6.95; N, 7.49. Found: C, 51.09; H, 6.88; N, 7.52.

EXAMPLE 5

3H,5H-Imidazo[1,5c]thiazole-7-carboxylic acid, tetrahydro-3,3-dimethyl-5-thioxo-1-pentyl,-,2,6-di-t-butyl-4-methylphenyl ester (1α,7α,7aα) and (1α,7β,7aα)

A procedure identical to that of Example 2 involving 2,2-dimethyl-5-pentyl-3-thiazoline and 2,6-di-t-butyl-4-methylphenyl-2-isothiocyanatoacetate afforded a 1:5 mixture (~90% yield) containing 3H,5H-imidazo[1,5c]-thiazole-7-carboxylic acid, tetrahydro-3,3-dimethyl-5-thioxo-1-pentyl-2,6-di-t-butyl-4-methylphenyl ester (1α,7α,7aα), mp 87°–95° C. IR (KBr) 3189, 2958, 1762; NMR (d, CDCL$_3$) 0.6–1.7 (29H, m, C(CH$_3$)$_3$, —CH$_2$, CH$_2$—CH$_3$), 1.9 (3H, s, CCH$_3$), 2.2 (3H, s, CCH$_3$), 2.3 (3H, s, phenyl methyl), 3.2–3.8 (1H, m, CHS), 4.3–4.9 (2H, m, CHN), 6.9 (1H, bs, NH), 7.1 (2H, bs, Ar—H).

Analysis Calculated for $C_{28}H_{44}N_2O_2S_2$: C, 66.62; H, 8.79; N, 5.55. Found: C, 66.60; H, 8.88; N, 5.52; and 3H,5H-imidazo[1,5c]thiazole-7-carboxylic acid, tetrahydro-3,3-dimethyl-5-thioxo-1-pentyl-,2,6-di-t-butyl-4-methylphenyl ester (1α,7β,7aα), mp 149–151. IR (KBr) 3447, 3177, 2958, 2924, 1760; NMR (d, CDCL$_3$) 0.57–2.2 (35H, m, C(CH$_3$)$_3$, -CH$_2$, -CH$_2$-CH$_3$, C(CH$_3$)$_2$), 2.3 (3H, s, Ar-H), 3.6–4.2 (1H, m, CHS), 4.3–5.0 (2H, M, CHN), 6.3–6.6 (1H, m, NH), 7.1 (2H, bS, Ar-H). Analysis Calculated for $C_{28}H_{44}N_2O_2S_2$: C, 66.62; H, 8.79; N, 5.55. Found: 66.56; H, 8.61; N, 5.60.

EXAMPLE 6

3H,5H-Imidazo[1,5c]thiazole-7-carboxylic acid, tetrahydro-3,3-pentamethylene-5-thioxo-1-pentyl,-ethyl ester (1α,7β,7aα).

To a dry tetrahydrofuran solution (600 ml) containing 2,2-pentamethylene-5-pentyl-3-thiazoline (123 mg, 0.548 mol) under a nitrogen atmosphere at −2° C. was added over a 10 minute period boron trifluoride etherate (67 ml, 0.548 mol). The reaction mixture was stirred at 0° for 15 minutes. The ice bath was removed, the reaction mixture was stirred for 45 minutes and was then cooled to −78° C. Lithium t-butoxide (48.5 g, 0.603 mol) was dissolved in dry tetrahydrofuran (800 ml) and the solution was cooled to −78° C. Ethyl isothiocyanatoacetate (87.5 g, 0.603 mol) was dissolved in dry tetrahydrofuran (250 ml) in a cold jacketed addition funnel (−78° C.) and was then added to the lithium t-butoxide solution over a 7 to 8 minute period. The internal temperature did not exceed −68° C. The solution was stirred for an additional 17 minutes at which time a polyethylene tube was used with positive nitrogen pressure to push the anion and the imine/boron trifluoride (−78° C.) solution. The addition occurred in about 3 minutes. The internal temperature rose from −78° to −55° C. The reaction mixture was stirred at −78° C. for 1.75 hour. and was then quenched with acetic acid (36 ml, 0.603 mol) in tetrahydrofuran (40 ml). The reaction mixture was concentrated in vacuo and the residue was taken up in ethyl acetate (3.25 liters) and washed with a 1:1 mixture of aqueous brine and saturated sodium bicarbonate (2 liters) followed by aqueous brine (1 liter). The organic portion was dried over magnesium sulfate, filtered and concentrated in vacuo to afford 212 g of oily solids. A hexane:ether (12:1) trituration afforded 88.1 g of mainly 3H,5H]1,5c]thiazole-7-carboxylic acid, tetrahydro-3,3-pentamethylene-5-thioxo-1-pentyl,-methyl ester [1α,7β,7aα). An additional 18.7 g was obtained by additional trituration of the mother liquor. An analytical sample, mp 121°–122° C. was obtained after carbon tetrachloride recrystallization. IR(KBr) 3429, 2930, 1741. NMR (d, CDCl$_3$) 0.8–2.2 (22H, m, CH$_2$, CH$_3$) 2.8–3.8 (3H, m, CHS, CCH$_2$), 4.1–4.9 (4H, m, OCH$_2$, CHN), 6.5 (1H, bS, NH) Analysis Calculated for $C_{18}H_{30}N_2O_2S_2$: C, 58.38; H, 8.11; N, 7.57. Found C, 58.18; H, 7.98; N, 7.74.

EXAMPLE 7

3H,5H-Imidazo[1,5c]thiazole-1-pentanoic acid, tetrahydro-7-carboethoxy-3,3-pentamethylene-5-thioxo, ethylester, (1α,7β,7aα).

To a dry tetrahydrofuran solution (40 ml) containing 2,2-pentamethylene-3-thiazoline-5-pentanoic acid, methyl ester (10.12 g, 37.6 mmol) under a nitrogen atmosphere at −10° C. was added over a 5 minute period period boron trifluoride etherate (4.63 ml, 13.6 mmol). The reaction mixture was stirred at 0° for 15 minutes. The ice bath was removed, the reaction mixture was stirred for 45 minutes and was then cooled to −78° C. Lithium t-butoxide (3.31 g, 41.4 mmol) was dissolved in dry tetrahydrofuran (50–75 ml) and the solution was cooled to −78° C. Ethy isothiocyanatoacetate (6.0 g, 41.4 mmol) was dissolved in dry tetrahydrofuran (240 ml) in a cold jacketed addition funnel (−78° C.) and was then added to the lithium t-butoxide solution over a 10 minute period. The internal temperature did not exceed −68° C. The solution was stirred for an additional 15 minutes at which time a polyethylene tube was used with positive nitrogen pressure to push the anion into the imine/boron trifluoride (−78° C.) solution. The addition including the washes occurred in about 3 minutes. The reaction mixture was stirred at −78° C. for 1.75 hour and was then quenched with acetic acid (2.5 ml, 41.4 mmol) in tetrahydrofuran (2 ml). The reaction mixture was concentrated in vacuo and the residue was taken up in ethyl acetate (250 ml) and washed with a 1:1 mixture of aqueous brine and saturated sodium bicarbonate (150 ml) followed by aqueous brine (75 ml). The organic portion was dried over magnesium sulfate, filtered and concentrated in vacuo to afford 15.6 g of a reddish brown oil which was triturated several times with a hexane:ether (10:1) solution to afford 8 g of mainly 3H,5H-imidazo[1,5c]thiazole-1-pentanoic acid, tetrahydro-7-carboethoxy-3,3-pentamethylene-5-thioxo, ethyl ester (1α,7β,7aα). An analytical sample, mp 84°–87° was obtained from a carbon tetrachloride recrystallization. IR(KBr) 3434, 2930, 1740, 1446, 1417 NMR(d, CDCl$_3$) 1.05–2.2 (19H, m, CH$_2$, C—CH$_3$), 2.2–2.6 (2H, m, CH$_2$), 3.2–3.6 (1H, m, CHS), 3.8 (3H, s, OCH$_3$), 4.2–5.0 (4H, m, CHN, OCH$_2$), 6.2–6.35 (1H, bs, NH).

EXAMPLE 8

3H,5H-Imidazo[1,5c]thiazole-7-carboxylic acid, tetrahydro-3,3-dimethyl-5-thioxo-1-pentyl; -methoxyethyl ester (1α,7α,7aα) and (1α,7β,7aα).

A procedure identical to that of Example 2 involving 2,2-dimethyl-5-pentyl-3-thiazoline and methoxyethyl isothiocyanatoacetate afforded after a pH 9 silica gel chromatography (eluant 98:2 methylene chloride:ether) a 1:2.9 mixture (85%) containing 3H,5H-imidazo[1,5c]thiazole-7-carboxylic acid, tetrahydro-3,3-dimethyl-5-thioxo-1-pentyl; methoxyethyl ester (1α,7α,7aα), mp 69°–70° C. IR(KBr) 3437, 2926, 1756. NMR(d, CDCL$_3$) 0.6–2.2 (17H, m, CH$_2$, CCH$_3$), 3.2–3.8 (6H, m, CHS, OCH$_2$, OCH$_3$) 4.1–4.8 (4H, m, CHN, OCH$_2$), 6.6–6.8 (1H, bs, NH). Analysis Calculated for $C_{16}H_{28}N_2S_2O_3$: C, 53.30; H, 7.83; N, 7.77. Found: C, 53.18; H, 7.56; N, 7.83; and 3H,5H-imidazo[1,5c]-thiazole-7-carboxylic acid, tetrahydro-3,3-dimethyl-5-thioxo-1-pentyl, methoxyethyl ester (1α,7β,7aα), mp 75°–77°. IR(KBr) 3437, 2926, 1756; NMR(d, CDCl$_3$) 0.6–2.4 (17H, m, CH$_2$, CCH$_3$) 3.0–3.8 (6H, m, CHS, OCH$_2$, OCH$_3$), 4.1–5.0 (4H, m, CHN, OCH$_2$), 6.7–7.0 (1H, bS, NH). Analysis calculated for $C_{16}H_{28}N_2S_2O_3$: C, 53.30; H, 7.83; N, 7.77. Found: C, 53.08; H, 7.70; N, 7.87.

EXAMPLE 9

3H,5H-Imidazo[1,5c]thiazole-7-carboxylic acid, tetrahydro-3,3-dimethyl-5-thioxo-1-pentyl, n-propyl ester, (1α,7α,7aα) and (1α,7β,7aα).

A procedure identical to that of Example 2 involving 2,2-dimethyl-5-pentyl-3-thiazoline and n-propyl isothiocyanatoacetate afforded after pH 9 silica gel chromatography (eluant 95:5 methylene chloride:ether) a 1:3 mixture (83% yield) containing 3H,5H-imidazo[1,5c]-thiazole-7-carboxylic acid, tetrahydro-3,3-dimethyl-5-thioxo-1-pentyl; n-propyl ester (1α,7α,7aα), mp 55°–56° C. IR(KBr) 3278, 2928, 1744; NMR(d, CDCL$_3$) 0.7–2.3 (22H, m, CH$_2$, CCH$_3$, CH$_2$CH$_3$), 3.2–3.7 (1H, m, CHS), 4.0–4.8 (4H, m, CHN, OCH$_2$), 6.5 (1H, bs, NH). Analysis calculated for C$_{16}$H$_{28}$N$_2$S$_2$O$_2$: C, 55.78; H, 8.19; N, 8.13. Found C, 55.81; H, 8.03; N, 8.06. and 3H,5H-imidazo-[1,5-c]thiazole-7-carboxylic acid, tetrahydro-3,3-dimethyl-5-thioxo-1-pentyl; n-propyl ester (1α,7β,7aα), mp 64°–66° C. IR(KBr) 3438, 2926, 1739; NMR(d, CDCL$_3$) 0.7–2.3 (22H, m, CH$_2$, CCH$_3$, CH$_2$CH$_3$), 3.1–3.5 (1H, m, CHS), 4.0–4.9 (4H, m, CHN, OCH$_2$), 6.6 (1H, bs, NH) Analysis calculated for C$_{16}$H$_{28}$N$_2$S$_2$O$_2$: C, 55.78; H, 8.19; N, 8.13 Found C, 55.71; H, 7.96; N, 8.08.

EXAMPLE 10

3H,5H-Imidazo[1,5c]thiazole-7-carboxylic acid, tetrahydro-3,3-dimethyl-5-thioxo-1-pentyl; isopropyl ester, (1α,7α,7aα) and (1α,7β,7aα).

A procedure identical to that of Example 2 including 2,2-dimethyl-5-pentyl-3-thiazoline and i-propyl-2-isothiocyanatoacetate afforded a 1:3 mixture (81% yield) containg 3H,5H-imidazo[1,5c]-thiazole-7-carboxylic acid, tetrahydro-3,3-dimethyl-5-thioxo-1-pentyl-, i-propyl ester (1α,7α,7aα), mp 103°–104° C. IR(KBr) 3210, 2956, 1737 NMR(d, CDCL$_3$) 0.6–2.5 (23H, m, CH$_2$, CH$_3$) 3.2–3.7 (1H, m, CHS), 4.0–5.4 (3H, m, CHN, CHO), 6.5–6.9 (1H, bs, NH). Analysis Calculated for C$_{16}$H$_{28}$N$_2$O$_2$S$_2$: C, 55.78; H, 8.19; N, 8.13. Found: C, 56.01; 8.08; N, 8.15; and 3H,5H-imidazo[1,5c]thiazole-7-carboxylic acid, tetrahydro3,3-dimethyl-5-thioxo-1-pentyl, i-propyl ester (1α,7β,7aα), mp 46°–49° C. IR(KBr) 3245, 2977, 2557, 1737. NMR(d, CDCl$_3$) 0.7–2.3 (23H, m, CH$_2$, CH$_3$), 3.1–3.6 (1H, m, CHS), 4.2 (1H, d, J=10 Hz, CHO), 4.5–5.4 (2H, m, CHN), 6.7 (1H, bs, NH), Analysis Calculated for C$_{16}$H$_{28}$N$_2$O$_2$S$_2$: C, 55.78; H, 8.19; N, 8.13. Found: C, 55.61; H, 7.90; N, 7.97.

EXAMPLE 11

3H,5H-Imidazo[1,5c]thiazole-7-carboxylic acid, tetrahydro-3,3-dimethyl-5-thioxo-1-pentyl, 2-methyl-6-t-butylphenyl ester (1α,7α,7aα) and (1α,7β,7aα).

A procedure identical to that of Example 2 involving 2,2-dimethyl-5-pentyl-3-thiazoline and 2-methyl-6-t-butylphenyl-2-isothiocyanatoacetate afforded a 1:3 mixture (90% yield) containing 3H,5H-imidazo[1,5c]-thiazole-7-carboxylic acid, tetrahydro-3,3-dimethyl-5-thioxo-1-pentyl-, 2-methyl-6-t-butylphenyl ester (1α,7α,7aα), mp 136°–138° C. IR(KBr) 3193, 2928, 1753: NMR(d, CDCL$_3$) 0.6–1.7 (20H, m, CH$_2$CH$_2$CH$_3$, C(CH$_3$)$_3$) 1.9 (3H, s, C—CH$_3$), 2.13 (3H, s, Ar—CH$_3$), 2.2 (3H, s, C—CH$_3$), 3.3–3.8 (1H, m, CHS), 4.4–5.0 (2H, m, CHN), 6.9 (1H, bs, NH), 7.1–7.4 (3H, m, Ar—H), Analysis Calculated for C$_{24}$H$_{36}$N$_2$O$_2$S$_2$: C, 64.25; H, 8.09; N, 6.24. Found: C, 64.27, H, 7.93, N, 6.41; and 3H,5H-imidazo[1,5c]thiazole-7-carboxylic acid, tetrahydro-3,3-dimethyl-5-thioxo-1-pentyl-, 2-methyl-6-t-butylphenyl ester (1α,7β,7aα), mp 142°–144° C. IR(KBr) 3217, 2925, 1745; NMR(d, CDCl$_3$) 0.7–1.8 (20H, m, CH$_2$, CH$_2$CH$_3$, C(CH$_3$)$_3$), 1.95 (3H, s, C—CH$_3$), 2.1 (3H, s, C—CH$_3$) 2.15 (3H, s, Ar—CH$_3$), 3.6–4.2 (1H, m, CHS), 4.3–4.9 (2H, m, CHN), 6.5 (1H, bs, NH), 7.0–7.4 (3H, m, Ar—H). Analysis calculated for C$_{24}$H$_{36}$N$_2$O$_2$S$_2$: C, 64.25; H, 8.09; N, 6.24. Found: C, 64.04; H, 7.93; N, 6.10.

EXAMPLE 12

3H,5H-imidazo[1,5c]thiazole-7-carboxylic acid, tetrahydro-3,3-pentamethylene-5-thioxo-1-pentyl (1α,7β,7aα).

To a tetrahydrofuran solution (30 ml) containing 3H,5H-imidazo[1,5c]thiazole-7-carboxylic acid, tetrahydro-3,3-pentamethylene-5-thioxo-1-pentyl, ethyl ester (1α,7β,7aα) (2.0 g, 5.4 mmol) at 0° C. was added 2N sodium hydroxide (3.1 ml, 6.2 mmol). The solution was stirred at 0° for 1 hour and allowed to stir at room temperature for 17 hours. Acetic acid (355 ml, 6.21 mol) was then added, the solution was concentrated in vacuo and dissolved in ethyl acetate (100 ml). The organic solution was extracted with 1N HCL (2×30 ml) and the aqueous solutions were back washed with ethyl acetate. The combined organic extracts were dried over magnesium sulfate, filtered and concentrated to afford 1.83 g (100%) of 3H,5H-imidazo-[1,5c]thiazole-7-carboxylic acid, tetrahydro-3,3-pentamethylene-5-thioxo-1-pentyl (1α,7β,7aα), NMR(d, CDCl$_3$ 0.62–2.3 (19H, m, CH$_2$, CH$_3$), 2.6–3.65 (3H, m, CHS, CCH$_2$), 4.05–4.85 (2H, m, CHN), 7.3 (1H, bs, NH), 10.65 (1H, bs, OH).

EXAMPLE 13

3H,5H-imidazo[1,5c]thiazole-7-carboxylic acid, tetrahydro-3,3-pentamethylene-5-thioxo-1-pentyl, methyl ester IS (1α,7β,7aα).

To an ether solution (20 ml) containing 3H,5H-imidazo[1,5c]thiazole-7-carboxylic acid, tetrahydro-3,3-pentamethylene-5-thioxo-1-pentyl (1α,7β,7aα) (761 mg, 2.22 mol) at 0° C. was added 99% d-ephedrine (371 mg, 2.22 mol). The solution was stirred for 12 hours at 0° C. and filtered. The solids were washed with ether, dried and recrystallized from benzene. The recrystallized salt was then placed in a methanol solution (30 ml) saturated with hydrochloric acid (0° C.) and stirred for 3 hours. The resultant solution was concentrated in vacuo, dissolved in ethyl acetate (50 ml) and washed with 2N hydrochloric acid (2×30 ml), dilute sodium bicarbonate (1×30 ml) followed by brine (1×30 ml) and dried over magnesium sulfate. The organic solution was filtered and concentrated in vacuo to afford 346 mg (61%) of 3H,5H-imidazo[1,5c]-thiazole-7-carboxylic acid, tetrahydro-3,3-pentamethylene-5-thioxo-1-pentyl, methyl ester IS (1α,7β,7aα)

NMR(d, CDCl$_3$) 0.7–2.4 (19H, m, CH$_2$, CH$_3$) 2.6–3.6 (3H, m, CHS, C—CH$_2$) 3.78 (3H, S, OCH$_3$). 4.0–4.9 (2H, m, CHN), 6.85 (1H, bs, NH).

EXAMPLE 14

3H,5H-imidazo[1,5c]thiazole, tetrahydro-3,3-pentamethylene-7-hydroxymethyl-5-thioxo-1-pentyl IS (1α,7β,7aα)

To a 1:1 tetrahydrofuran:methanol solution (8 ml) containing 3H5H-imidazo[1,5c]thiazole-7-carboxylic acid, tetrahydro-3,3-pentamethylene-5-thioxo-1-pentyl, methyl ester 1S (1α,7β,7aα) (657 mg, 1.85 mmol) was added sodium borohydride (274 mg, 7.4 mol). The solution was stirred at 0° C. for 1.5 hour, at room temperature for 1.5 hour and concentrated under reduced pressure. Ethyl acetate (75 ml) was added to the residue and the organic solution was extracted with 0.5N HCL (1×40 ml) and a 1:1 brine:sodium bicarbonate solution (1×40 ml). The organic layer was dried over magnesium sulfate; filtered and concentrated in vacuo to afford 580 mg (100%) of 3H,5H-imidazo[1,5c]thiazole, tetrahydro3,3-pentamethylene-7-hydroxymethyl-5-thioxo-1-pentyl IS (1α,7β,7aα).

NMR(d, CDCl3) 0.6–2.2 (19H, m, CH2, CH3), 2.7–4.7 (7H, m, CH2—O, CHN, CHS, OH, C—CH2), 7.05 (1H, bs, NH).

EXAMPLE 15

3H,5H-Imidazo[1,5c]thiazole-1-pentanoic acid, tetrahydro-3,3-dimethyl-7-hydroxymethyl-5-thioxo, methyl ester, (1α,7β,7aα)

To a methanol solution (150 ml) containing 3H,5H-imidazo[1,5c]thiazole-1-pentanoic acid, tetrahydro-7-carboethoxy-3,3-dimethyl-5-thioxo, methyl ester (1α,7β,7aα) (5.64 g, 15.08 mmol) at 0° C. was added sodium borohydride (2.28 g, 60.32 mmol). The solution was stirred to 0° C. for 1.75 hour, and allowed to warm to room temperature (45 minutes). The reaction mixture was concentrated in vacuo and taken up in ethyl acetate (300 ml). The organic solution was extracted with 0.2N HCL (70 ml) and a brine solution (70 ml), dried over magnesium sulfate, filtered and concentrated in vacuo to afford 5.0 g (99%) of 3H,5H-imidazo[1,5c]thiazole-1-pentanoic acid, tetrahydro-3,3-dimethyl-7-hydroxymethyl-5-thioxo, methyl ester (1α,7β,7aα). An analytical sample, mp 103°–10°, was prepared by an ether recrystallization. IR(KBr) 3411, 3199, 2927, 1731. NMR(d, CDCL3) 0.7–2.6 (14H, m, CH2), 3.66 (3H, s, OCH3), 2.9–4.9 (6H, m, CHN, CHS, CH2—O, OH), 6.8—7.1 (1H, bs NH). Analysis Calculated for C14H24N2O3S2: C, 50.60; H, 7.23; N, 8.43. Found: C, 50.36; H, 7.08; N, 8.49.

EXAMPLE 16

3H,5H-Imidazo[1,5c]thiazole, tetrahydro-3,3-dimethyl-7-hydroxymethyl-5-thioxo-1-pentyl, (1α,7β,7aα)

3H,5H-Imidazo[1,5c]thiazole-7-carboxylic acid, tetrahydro-3,3-dimethyl-5-thioxo-1-pentyl-, ethyl ester (1α,7β,7aα) (572 mg,1.73 mol) was dissolved in methanol (15 ml) and cooled to 0° C. Sodium borohydride (262 mg, 6.93 mol) was added and the solution was stirred at 0° for 1.75 hr and allowed to come to room temperature. The reaction mixture was concentrated in vacuo and taken up in ethyl acetate (75 ml). The organic solution was extracted with 0.05N HCL (1×40 ml) and a 1:1 brine:sodium bicarbonate solution (1×80 ml). The organic layer was dried over magnesium sulfate, filtered and concentrated in vacuo to afford 486 mg (97%) of 3H,5H-Imidazo[1,5c]thiazole, tetrahydro-3,3-dimethyl-7-hydroxymethyl-5-thioxo-1-pentyl (1α,7β,7aα). An analytical sample, mp 112°–114° C. was obtained following a methanol recrystallization. IR(KBr) 3351, 2925; NMR(d, CDCL3) 0.4–2.5 (17H, m, C—CH2, CH3), 3.2–4.8 (6H, m, CHS, CHN, CH2O, OH), 6.9–7.2 (1H, m, NH) Analysis Calculated for C13H24N2OS2: C, 54.17; H, 8.33; N, 9.72. Found: C, 54.26; H, 8.07; N, 9.55.

EXAMPLE 17

3H,5H-Imidazo[1,5c]thiazole-1-pentanoic acid, tetrahydro-3,3-dimethyl-7-[[(methylsulfonyl)oxy]methyl]-5-oxo, methyl ester, (1α,7β,7aα)

To a methylene chloride solution (10 ml) containing 3H,5H-imidazo[1,5c]thiazole-1-pentanoic acid, tetrahydro-3,3-dimethyl-7-hydroxymethyl-5-oxo, methyl ester (1α,7β,7aα). (220 mg, 0.695 mmol) at 0° C. was added triethylamine (200 μl, 1.42 mol, followed by methanesulfonyl chloride (621 μl, 0.775 mmol). The solution was allowed to warm to room temperature and stirred for 1 hour. Additional methylene chloride (50 ml) was added and the organic solution was extracted with H2O (1×30 ml), 0.5N HCL (1×20 ml), 5% sodium bicarbonate (1×20 ml) and brine (1×20 ml) The aqueous layers were backwashed with methylene chloride and the organic extracts were dried over magnesium sulfate, filtered and concentrated in vacuo to give 263 mg (96%) of 3H,5H-imidazo[1,5c]thiazole-1-pentanoic acid, tetrahydro-3,3-dimethyl-7-[[(methylsulfonyl)oxy]methyl]-5-oxo, methyl ester (1α,7β,7aα). An analytical sample, mp 118.5°–119.5° C. was obtained following an ether recrystallization.

IR(KBr) 3305, 1732, 1711. NMR(d, CDCL3) 1.0–2.0 (12H, m, C—CH2, C(cH3)2), 2.1–2.5 (2H, t,

CH2—C), 3.1 (3H, s,

CH3—S), 3.4–4.6 (8H, m, OCH3, CH2—O, CHN, CHS), 5.6–5.9 (1H, m, NH). Analysis Calculated for C15H26N2O6S2: C, 45.68; H, 6.60; N, 7.11 Found: C, 45.90; H, 6.45; N, 7.08.

EXAMPLE 18

3H,5H-Imidazo[1,5c]thiazole, tetrahydro-3,3-pentamethylene-7-[[(d-camphorsulfonyl)oxy]methyl]-5-thioxo-1-pentyl IS (1α,7β,7aα)

To a methylene chloride solution (100 ml) containing 3H,5H-imidazo[1,5c]thiazole, tetrahydro-3,3-pentamethylene-7-hydroxymethyl-5-thioxo-1-pentyl (1α,7β,7aα) (3.78 g, 11.5 mmol) at 0° C. was added triethylamine (1.61 ml, 11.5 mol) followed by d-10-camphorsulfonyl chloride (2.89 g, 11.5 mmol) in methylene chloride (25 ml). The reaction mixture was stirred for 2 hr at 0° C. Additional methylene chloride (400 ml) was added and the reaction mixture was washed with brine (1×100 ml), dried over magnesium sulfate, filtered and concentrated in vacuo to afford a solid which was chromatographed on 500 g of 48–63μ silica gel using ether:-methylene chloride (4:96). A total of 4.46 g (71%) of diasteriometric products was obtained. The first isomer (2.23 g) was 3H,5Himidazo[1,5c]thiazole, tetrahydro-3,3-pentamethylene-7-[[(d-camphorsulfonyl)oxy]methyl]-5-thioxo-1-pentyl IS C=0.01, (1α,7β,7aα) $\alpha D = +14.9$ (methanol). NMR(d, CDCL$_3$) 0.8 (3H, s, CCH$_3$), 1.0 (3H, s, CCH$_3$), 0.8–2.5 (28H, m, CH$_2$, C—CH, CH$_2$CH$_3$), 3.25 (2H, q CH$_2$SO$_2$), 3.0–3.7 (1H, m, CHS), 3.7–4.7 (4H, m, CHN, CH$_2$—O), 6.28 (1H, bs, NH).

EXAMPLE 19

Dl-Biotin, methyl ester

To a trifluoroacetic acid solution (10 ml) containing 3H,5H-imidazo[1,5c]thiazole-1-pentanoic acid, tetrahydro-3,3-dimethyl-7-[[(methylsulfonyl)oxy]methyl]-5-oxo, methyl ester (1α,7β,7aα) (263 mg, 0.67 mmol) was added deuterium oxide (0.6 ml). The solution was heated at 45° C. for 5 hours (reaction was monitored by NMR) and then concentrated in vacuo. The crude reaction mixture was dissolved in methylene chloride (200 ml) and extracted with dilute sodium bicarbonate (1×50 ml) followed by brine (1×50 ml). The aqueous extracts were back extracted with methylene chloride (100 ml) and the combined orange extracts were dried over magnesium sulfate, filtered and concentrated under reduced pressure to give 183 mg of crude solid which was triturated with ether and recrystallized from ethyl acetate to give 78 mg (43%) or dl-biotin methyl ester, mp 127°–129° C. IR(KBr) 3225, 2941, 1751, 1718. NMR(d, DMSO) 1.15–1.95 (6H, m, CH$_2$), 2.35 (2H, t, CH$_2$—CO), 2.60–3.06 (2H, m, CH$_2$S) 3.08–3.30 (1H, m, CHS), 3.65 (3H, s, OCH$_3$), 4.15–4.64 (2H, m, CHN), 5.90 (1H, bs, NH), 6.13 (1H, bs, NH) Analysis Calculated for C$_{11}$H$_{18}$N$_2$O$_3$S: C, 51.16; H, 6.98; N, 10.85. Found: C, 51.17; H, 7.01; N, 10.85. Mass Spectrum: Calculated (258.1038), observed (258.1041).

EXAMPLE 20

1-H-Thieno[3,4-d]imidazole-4-pentanoic acid, hexahydro-2-thioxo (3aα,4β,6aα) (dl-thioxobiotin)

A trifluoroacetic acid solution (2 ml) containing 3H 5H-imidazo[1,5c]thiazole, tetrahydro-3,3-pentamethylene-7-hydroxymethyl-5-thioxo-1-pentyl (1α,7β,7aα) (302 mg, 0.812 mmol) and water (0.86 ml) was heated under reflux for 1.5 hours and then cooled to 50° C. and concentrated in vacuo. Ethanol (5 ml) was added and the solution was again concentrated under reduced pressure. The solid residue was triturated with diisopropylether and then ethyl acetate to afford 134 mg (64%) of 1-H-thieno[3,4-d]imidazole-4-pentanoic acid, hexahydro-2-thioxo (3aα,4β,6aα) (dl-thioxobiotin) mp>250°. IR(KBr) 3407, 3291, 2939, 1694. NMR(d, DMSO) 1.22–1.77 (6H, m, CH$_2$), 2.33 (2H, t, J=8 Hz, CH$_2$—CO), 2.68 (1H, d, J=12 Hz, CH$_2$S), 2.90 (1H, q, J$_{AB}$=12 HZ, Jax=6 HZ, CH$_2$S), 3.15–3.25 (1H, m, CHS), 4.35–4.50 (1H, m, CHN) 4.53–4.64 (1H, m, CHN), 8.21 (1H, bs, NH), 8.31 (1H, bs, NH). Analysis Calculated for C$_{10}$H$_{16}$N$_2$O$_2$S$_2$: C, 46.15; H, 6.15; N, 10.77, Found: C, 46.52; H, 6.19; N, 10.48.

EXAMPLE 21

1-H-Thieno[3,4-d]imidazole-hexahydro-2-thioxo-4-pentyl; 3aS (3aα,4β,6aα)

3H,5Himidazo[1,5c]thiazole, tetrahydro-3,3-pentamethylene-7-[[(d-camphorsulfonyl)oxy]methyl]-5-thioxo-1-pentyl IS (1α,7β,7aα) (761 mg, 1.40 mmol) was dissolved in trifluoroacetic acid (5 ml). Water (1 ml) was added and the solution was kept at 45° for about 17 hours. The reaction mixture was concentrated in vacuo. The white solid residue was dissolved in boiling ethyl acetate (500 ml), aqueous sodium bicarbonate (100 ml) was added and the hot two phase system was separated. The organic portion was dried over magnesium sulfate, filtered and concentrated in vacuo to afford, after a methanol trituration, 187 mg (58%) of 1-H-thieno[3,4-d]imidazolehexahydro-2-thioxo-4-pentyl 3aS (3aα,4β,6aα), mp 262°–262.5° C.; α$_D$= +133° (C=0.01, TFA); IR (KBr) 3220, 2919; NMR (d, DMSO) 0.68–1.04 (3H, m, CH$_2$CH$_3$), 1.08–1.96 (8H, m, C—CH$_2$), 2.64–2.98 (2H, m, CH$_2$S), 3.05–3.36 (1H, m, CHS), 4.28–4.46 (1H, m, CHN), 4.47–4.70 (1H, m, CHN), 8.14 (1H, bs, NH), 8.22 (1H, bs, NH). Analysis calculated for C$_{10}$H$_{18}$N$_2$S$_2$: C, 52.17; H, 7.83; N, 12.17. Found C, 51.93; H, 7.44; N, 12.09.

EXAMPLE 22

1H-Thieno[3,4-d]imidazole-hexahydro-2-thioxo-4-pentyl; 3aS (3aα,4β,6aα).

3H,5H-imidazo[1,5-c]thiazole, tetrahydro-3,3-pentamethylene-7-hydroxymethyl-5-thioxo-1-pentyl 1S (1α,7β,7aα) (580 mg, 1.77 mmol) was dissolved in trifluoroacetic acid (4.6 ml) and water (1.2 ml) and the resultant solution was heated at 100°–105° C. for 4 hours. The reaction mixture was cooled to 50° C. and concentrated in vacuo. Ethanol (6.0 ml) was added and the solution was again concentrated under reduced pressure. The white residue was triturated with ethyl acetate to afford 267 mg (66%) of 1H-thieno[3,4-d]imidazole-hexahydro-2-thioxo-4-pentyl, 3aS (3aα,4β,6aα), mp 262–262.5α$_D^{25°}$ $C$=133° (C=0.01, TFA); IR (KBr) 3220, 2919; NMR (d, DMSO) 0.68–1.04 (3H, m, CH$_2$CH$_3$), 1.08–1.96 (8H, m, C—CH$_2$), 2.64–2.98 (2H, m, CH$_2$S), 3.06–3.36 (1H, m, CHS), 4.28–4.46 (1H, m, CHN), 4.47–4.70 (1H, m, CHN), 8.14 (1H, bs, NH), 8.22 (1H, bs, NH).

EXAMPLE 23

1-H-Thieno[3,4-d]imidazole-hexahydro-2-oxo-4-pentyl; (3aα,4β,6aα).

To an ethanol solution (14 ml) containing 1-H-thieno[3,4d]imidazole-hexahydro-2-thioxo-4-pentyl (3aα,4β,6aα) (307 mg, 1.33 mmol) was added bromoethanol (208 ml, 2.93 mol). The solution was heated under reflux for 20 hours. Aqueous saturated sodium carbonate (1.5 ml) was added and the reaction was heated for an additional 10 minutes, cooled, and concentrated in vacuo to give a solid residue which was dissolved in ethyl acetate (100 ml) and shaken with brine (2×35 ml). The organic extract was dried over magnesium sulfate, filtered and concentrated in vacuo to afford white solids which were recrystallized from ethyl acetate to give 196 mg (69%) of 1-H-thieno[3,4-d]imidazole-hexahydro-2-oxo-4-pentyl (3aα,4β,6aα) mp 144°–145° C. IR(KBr) 3175, 2899, 1709; NMR (d, DMSO) 0.69–1.10 (3H, m, CH$_3$), 1.11–1.86 (8H, m, CH$_2$), 2.44–2.96 (2H, m, CH$_2$-S), 2.98–3.24 (1H, m, CHS), 4.02–4.21 (1H, m, CHN), 4.30–4.44 (1H, m, CHN), 6.36 (1H, bs, NH), 6.58 (1H, bs, NH); Mass spectrum: Calculated 214.1140, Observed: 214.1144. Analysis Calculated for C$_{10}$H$_{18}$N$_2$OS: C, 56.08; H, 8.41; N, 13.08. Found C, 56.00; H, 8.07; N, 12.71.

EXAMPLE 24

(dl-Biotin)

A diglyme solution (3 ml) containing dl-thioxobiotin (255 mg, 0.981 mol) and bromoethanol (140 μl, 1.98 mmol) was allowed to reflux (150°) for 2.5 hours. The solution was cooled, dilute sodium carbonate (50 ml) was added, and the solution was extracted with hexane (50 ml). The pH of the aqueous phase was adjusted to 1.5 with 6N HCL and extracted with ethyl acetate (4×100 ml). The ethyl acetate extract was dried over magnesium sulfate, filtered and concentrated in vacuo to give 148 mg (62%) of crude biotin, mp 220°–223° C. which was recrystallized from water IR (KBr) 3279, 2899, 1724; NMR (d, DMSO) 0.76–1.95 (6H, m, C—$CH_2$), 2.00–2.40 (2H, t, $CH_2$—CO), 2.70–2.98 (1H, m, $CH_2$S) 3.00–3.54 (2H, m, $CH_2$S, CHS) 4.00–4.44 (2H, m, CHN), 6.44 (1H, bs, NH), 6.55 (1H, bs, NH), 11.8–12.4 (1H, bs, OH). Analysis calculated for $C_{10}H_{16}O_3N_2S$: C, 49.18; H, 6.56; N, 11.48; Found: C, 49.30; H, 6.23; N, 11.37. Mass spectrum: calculated: 244.0880, found: 244.0925.

EXAMPLE 25

2,2-Dimethyl-5-pentyl-3-thiazoline

The procedure of M. Thiel, F. Asinger, K. Schmiedel, (Liebigs Ann. Chem. 611, 121 (1958)) was employed. To a methanol solution (3 liters) containing sodium methoxide (216.7 g, 4.01 mole) at −10° C. was added hydrogen sulfide (∼1 lb) until the solution was saturated. To this solution was added dropwise over a 2 hour period 2-bromoheptaldehyde (775 g, 4.01 mol). The temperature of the reaction was maintained at about −10° C. after the addition, acetone (734 g, 12.6 mole) was added over a 10 minute period and the solution was stirred for an additional 20 minutes at about −10° C. at which time ammonia was added over a period of 1.5 hours. The solution was then poured into water (4 liters) and extracted with ether (4×1 liter). The combined etheral extracts were washed with brine (1×1 liter), dried over magnesium suflate and concentrated in vacuo to afford after distillation (70°–80°/1.5 mm) 549 g (74%) of 2,2-dimethyl-5-pentyl-3-thiazoline. ;NMR (d, $CDCl_3$) 0.6–2.2 (11H, m, $CH_2,CH_3$) 1.70 (6H, s, $C(CH_3)_2$), 4.3–4.65 (1H, m, CHS), 7.10 (1H, d, CHN).

EXAMPLE 26

3-Thiazoline-5-pentanoic acid, 2,2-dimethyl, methyl ester

The procedure of M. Thiel, F. Asinger, K. Schmiedel, (Liebigs Ann. Chem. 611, 121 (1958)) was employed. A sodium methoxide solution was prepared by adding sodium (736 mg, 32 mmol) to methanol (30 ml) under a nitrogen atmosphere. This solution was cooled to −10° C. and saturated with hydrogen sulfide (∼20 minutes). To this solution was added dropwise over a 15 minute period 5-bromo-6-formylhexanoic acid, methyl ester (7.49 g, 32 mmol). The reaction temperature was kept below −10° C. This solution was stirred for an additional 5 minutes at −10° C. at which time acetone (8 ml), was added. The reaction was stirred at −10° for 10 minutes at which time ammonia was introduced. The reaction temperature was not allowed to exceed 25° C. The reaction mixture became clear and ammonia was bubbled into the solution for about 40 minutes. Water (100 ml) was then added and this solution was extracted with ether (4×100 ml). The organic layer was dried over magnesium sulfate, filtered, and concentrated in vacuo to afford, after distillation (116°–125°/0.25 mm) 6.19 g (85%) of 3-thiazoline-5-pentanoic acid, 2,2-dimethyl, methyl ester. IR ($CHCL_3$) 2944, 1734 1648. NMR (d, $CDCL_3$) 1.2–2.1 (12H, m, C—$CH_2$, $C(CH_3)_2$), 2.2–2.5 (2H, m, $CH_2CO$), 3.7 (3H, s, $OCH_3$), 4.2–4.7 (1H, m, CHS), 7.0–7.2 (1H, m, CHN).

EXAMPLE 27

2,2-pentamethylene-5-pentyl-3-thiazoline

The procedure of M. Thiel, F. Asinger, K. Schmiedel, (Liebigs Ann. Chem. 611, 121 (1958)) was employed. To a methanol solution (75 ml) containing sodium hydrogen sulfide-water (6.25 g, 67.9 mmol) at −10° to 15° C. was added over a 15 minute period a methanol solution (15 ml) containing 2-bromoheptaldehyde (13.1 g, 67.9 mol). The temperation of the reaction mixture was maintained at about −10° C. After stirring for 15 minutes, cyclohexanone (21.1 ml, 204 mmol) was added over a period of 2 minutes. This solution was stirred for an additional 15 minutes at −10° C. at which time ammonia was introduced. Ammonia was added over a one hour period and the reaction mixture was allowed to warm to room temperature. The clear solution was poured into water (250 ml) and extracted with ether (3×200 ml). The organic extract was dried over magnesium sulfate, concentrated in vacuo and distilled (115°–125°/0.15 mm) to afford 10 g (66%) of 2,2-pentamethylene-5-pentyl-3-thiazoline. IR ($CHCl_3$) 2900, 2830, 1648, 1530; NMR (d, $CDCL_3$) 0.68–2.9 (21H, m, $CH_2$, $CH_3$), 4.15–4.50 (1H, m, CHS), 7.2 (1H, d, CHN).

EXAMPLE 28

1H-Thieno[3,4-d]imidazole-hexahydro-2-oxo-4-pentyl, (3aα,4β,6aα).

To a methanol solution (20 ml) containing 3H,5H-imidazo[1,5c]thiazole-7-carboxylic acid, tetrahydro-3,3-dimethyl-5-oxo-1-pentyl, ethyl ester (1α,7β,7aα) (358 mg, 1.14 mol) was added potassium hydroxide (75 mg, 1.14 mmol) in water (20 ml). The solution was stirred for 3 hours at room temperature, concentrated in vacuo, dissolved in ethyl acetate (200 ml) and extracted with 6N HCL (50 ml). The organic extract was dried over magnesium sulfate, filtered and concentrated under reduced pressure to give 330 mg of crude 3H,5H-imidazo[1,5-c]thiazole. 7-carboxylic acid, tetrahydro-3,3-dimethyl-5-oxo-1-pentyl (1α,7β,7aα). IR (KBr), 3359, 2927, 1733; NMR (d, DMSO) 0.7–2.3 (17H, m, $CH_2$, $CH_3$), 3.0–4.7 (3H, m, CHN, CHS), 6.7–7.03 (1H, m, NH). This acid was dissolved in trifluoroacetic acid (10 ml), deuterium oxide (0.6 ml) was added and the solution was heated at 45° C. for 15 hours. The reaction mixture was concentrated in vacuo, taken up in ethyl acetate (200 ml) washed with water (2×50 ml), dried over magnesium sulfate, filtered, concentrated in vacuo, and precipitated with 1:1 methylene chloride: ether to afford 125 mg of crude 1H-thieno[3,4-d]imidazole-2,4-dione, tetrahydro-6-pentyl-, (3aα,6β,6aα). An analytical sample, mp 247–247.5 was obtained after a hexane:methylene chloride recrystallization. IR (KBr) 3333, 2899, 1695. NMR (d, $CDCL_3$) 0.62–1.02 (3H, m, $CH_3$), 1.11–2.02 (8H, m, $CH_2$), 3.92–4.53 (3H, m, CH), 6.66–6.90 (1H, m, NH), 7.30–7.56 (1H, m, NH). Analysis Calculated for $C_{10}H_{16}N_2O_2S$: C, 52.63; H, 7.02; N, 12.28. Found: C, 52.30; H, 7.00; N, 12.28. This lactone (174 mg, 0.76 mmol) was dissolved in methanol (15 ml) at 0° C. Sodium borohydride (114 mg, 3.05 mmol) was added and the reaction mixture was allowed to warm to room temperature, stirred for an additional 1 hour and was then concentrated in vacuo. The residue was taken up in ethyl acetate (50 ml) and washed with water (1×20 ml), brine (1×20 ml), dried over magnesium sulfate, filtered and concentrated to afford 70 mg of a white solid which was dissolved in acetic acid (15 ml) and treated with zinc (excess) at room temperature (4 hours), 40° C. (2 hours) and at reflux (3 hours). Thin layer chromatography (90:10:1 chloroform:methanol:ammonium hydroxide) indicated the formation of 1-$\underline{\text{H}}$-thieno[3,4-d]imidazole-hexahydro-2-oxo-4-pentyl (3a$\alpha$,4$\beta$,6a$\alpha$).

EXAMPLE 29

1$\underline{\text{H}}$-thieno[3,4-$\underline{\text{d}}$]imidazole-2,4-dione, tetrahydro-6-pentyl (3a$\alpha$,6$\beta$,6a$\alpha$).

To a methanol solution (20 ml) at 5° C. containing 3$\underline{\text{H}}$,5$\underline{\text{H}}$-imidazo[1,5c]thiazole-7-carboxylic acid, tetrahydro-3,3-dimethyl-5-oxo-1-pentyl, ethyl ester (1$\alpha$,-7$\alpha$,7a$\alpha$) (629 mg, 2.0 mmol) was added potassium hydroxide (129 mg, 2.0 mmol) in water (2 ml). The reaction mixture was stirred for 1 hour at room temperature, acidified to pH 3 with 1N HCL, extracted with ethyl acetate (3×100 ml), dried over magnesium sulfate, filtered and concentrated in vacuo to afford a white solid which was triturated with hexane:ether to give 327 mg of crude 3$\underline{\text{H}}$,5$\underline{\text{H}}$-imidazo[1,5c]thiazole-7-carboxylic acid, tetrahydro-3,3-dimethyl-5-oxo-1-pentyl (1$\alpha$,7$\alpha$,-7a$\alpha$) mp 210°–211° C. IR (KBr) 3359, 2927, 1733; NMR (DMSO) 0.7-2.3 (17H, m, CH$_2$, CH$_3$), 3.0–4.7 (3H, m, CH) 6.7-7.03 (1H, m, NH). Analysis Calculated for C$_{13}$H$_{22}$N$_2$O$_3$S: C, 54.52; H, 7.74; N, 9.78. Found C, 54.50; H, 7.67; N, 10.05. This acid was dissolved in trifluoroacetic acid (4 ml), deuterium oxide (1 ml) was added and the solution was stirred at room temperature for 2 hours. The reaction mixture was concentrated in vacuo (3×) (toluene was used to azeotrope off water) to afford 289 mg of crude thiol which was placed in dry methylene chloride (125 ml) in the presence of triethylamine (170 ml, 1.22 mol) at 0° C. Ethylchloroformate (117 ml, 1.22 mmol) was added and the reaction mixture was stirred for 2 hours at room temperature. The solvent was then concentrated under reduced pressure, and the white residue was taken up in ethyl acetate (80 ml)). The organic solution was washed with water (40 ml), dried over magnesium sulfate, filtered, and concentrated in vacuo to afford 270 mg of solids which were recrystallized from ethyl acetate to afford 110 mg of 1H-thieno[3,4-d]imidazole-2,4-dione, tetrahydro-6-pentyl (3a$\alpha$,6$\alpha$,6a$\beta$), mp 177°-180° C. IR (KBr) 3125, 2890, 1786, 1670. Analysis Calculated for C$_{10}$H$_{16}$N$_2$O$_2$S: 52.63; H, 7.02; N, 12.28. Found: 52.88; H, 7.15; N, 12.22. This thiolactone (21 mg, 0.09 mmol) was dissolved in tetrahydrofuran (2 ml), DBU 1,8-diazabicyclo[5.4.0]-undec C-7 ene (1.38 µl, 0.009 mmol) was added and the solution was stirred for 20 minutes. IN HCL (100 1, 0.1 mol) was added and the reaction mixture was concentrated under reduced pressure, taken up in ethyl acetone (50 ml) and extracted with water. The organic layer was dried over magnesium sulfate, filtered and concentrated in vacuo to afford 21 mg of 1H-thieno-[3,4d]imidazole-2,4-dione, tetrahydro-6-pentyl-(3a$\alpha$,6$\beta$,6a$\alpha$).

I claim:

1. A compound of the formula

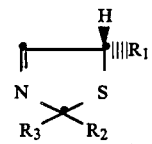

or a boron trifluoride adduct thereof, wherein

R$_1$ is —(CH$_2$)$_4$CH$_3$,

—(CH$_2$)$_3$OR or —(CH$_2$)$_5$OR wherein R is alkyl,

—(CH$_2$)$_4$CN, or

—(CH$_2$)$_4$COOR' wherein R' is alkyl or phenyl;

R$_2$ and R$_3$ when taken together are cycloalkyl or —CH$_2$—CH$_2$—Y—CH$_2$—CH$_2$ wherein Y is sulfur, oxygen or NR" wherein R" is COOR''' wherein R''' is alkyl, or R$_2$ and R$_3$ when taken separately are each alkyl, cycloalkyl or phenyl provided that R$_2$ and R$_3$ are not both phenyl;

said alkyl having from 1 to 4 carbon atoms and said cycloalkyl having from 5 to 7 carbon atoms.

2. A boron trifluoride adduct of claim 1.

3. A compound of claim 1 wherein

R$_1$ is

—(CH$_2$)$_4$CH$_3$ or —(CH$_2$)$_4$COOR' wherein R' is alkyl; and

R$_2$ and R$_3$ when taken together are cycloalkyl, or

R$_2$ and R$_3$ when taken separately are each alkyl.

4. A compound of claim 3 wherein

R$_1$ is —(CH$_2$)$_4$CH$_3$ or —(CH$_2$)$_4$COOCH$_3$; and

R$_2$ and R$_3$ when taken together are cyclohexyl, or

R$_2$ and R$_3$ when taken separately are each methyl.

5. A compound of claim 4 wherein R$_1$ is —(CH$_2$)$_4$CH$_3$ and R$_2$ and R$_3$ when taken together are cyclohexyl.

* * * * *